(12) United States Patent
Bonadeo et al.

(10) Patent No.: US 8,744,160 B2
(45) Date of Patent: Jun. 3, 2014

(54) SYSTEMS AND METHODS FOR MEASUREMENT OF GEOMETRICAL PARAMETERS OF THREADED JOINTS

(75) Inventors: Nicolas Hernan Bonadeo, Buenos Aires (AR); Sebastian Berra, Buenos Aires (AR); Javier Ignacio Etcheverry, Buenos Aires (AR)

(73) Assignee: Tenaris Connections Limited, Kingstown (VC)

( * ) Notice: Subject to any disclaimer, the term of this patent is extended or adjusted under 35 U.S.C. 154(b) by 352 days.

(21) Appl. No.: 13/151,202

(22) Filed: Jun. 1, 2011

(65) Prior Publication Data

US 2011/0293169 A1 Dec. 1, 2011

(30) Foreign Application Priority Data

Jun. 1, 2010 (EP) .................................. 10164636

(51) Int. Cl.
*G06K 9/00* (2006.01)
*A61B 6/02* (2006.01)
*G06T 11/00* (2006.01)

(52) U.S. Cl.
CPC .............. *A61B 6/027* (2013.01); *G06T 11/005* (2013.01)
USPC ............................................. 382/131; 378/9

(58) Field of Classification Search
USPC ....................................................... 382/141
See application file for complete search history.

(56) References Cited

U.S. PATENT DOCUMENTS

| 3,489,437 | A | 1/1970 | Duret |
| 4,644,394 | A | 2/1987 | Reeves |
| 5,136,157 | A | 8/1992 | Apter et al. |
| 5,137,310 | A | 8/1992 | Noel et al. |
| 5,260,780 | A | 11/1993 | Staudt, III |
| 5,521,707 | A * | 5/1996 | Castore et al. ................ 356/394 |
| 5,712,706 | A | 1/1998 | Castore et al. |

(Continued)

FOREIGN PATENT DOCUMENTS

| GB | 1 398 214 | 6/1973 |
| GB | 1 428 433 | 3/1976 |

(Continued)

OTHER PUBLICATIONS

Albion Devices, Inc., "Why Compensate for Temperature?" Albion Devices, Inc., Feb. 2004.
International Preliminary Report on Patentability in corresponding International Application No. PCT/EP2009/066309, issued Jun. 7, 2011.

(Continued)

*Primary Examiner* — Hadi Akhavannik
(74) *Attorney, Agent, or Firm* — Knobbe Martens Olson & Bear, LLP

(57) ABSTRACT

Thread parameters for a threaded object are determined. Spatial reference systems (X, Y, Z) and (X', Y', Z') are respectively identified for a position sensor and the threaded object. A transformation matrix describing a quadratic form representing the threaded object in (X, Y, Z) may be determined to relate the reference systems. For example, a sensor trajectory on the threaded object may be determined, along with measurement points on the threaded object. The measurement points may be selected so the matrix, evaluated on these values, has maximum rank. Position data at measurement points in the second reference system may be transformed into the first reference system, yielding first results. After coating the threaded object, position data at the measurement points may be acquired again and transformed into the first reference system, yielding second results. Comparisons between the first and second results may provide thickness of the coating and quality verification.

23 Claims, 10 Drawing Sheets

(56) References Cited

U.S. PATENT DOCUMENTS

| | | | |
|---|---|---|---|
| 5,871,391 | A | 2/1999 | Pryor |
| 7,310,890 | B2 | 12/2007 | Cattaneo et al. |
| 2005/0134838 | A1 | 6/2005 | Hartmann et al. |
| 2008/0158905 | A1 | 7/2008 | Chuang et al. |
| 2009/0033087 | A1* | 2/2009 | Carcagno et al. ............... 285/55 |
| 2010/0110448 | A1 | 5/2010 | Johnson |
| 2011/0084483 | A1* | 4/2011 | Nunez ........................... 285/334 |
| 2011/0238199 | A1 | 9/2011 | Bonadeo et al. |
| 2011/0293169 | A1 | 12/2011 | Bonadeo |
| 2011/0295550 | A1 | 12/2011 | Bonadeo |

FOREIGN PATENT DOCUMENTS

| | | |
|---|---|---|
| WO | WO 2004/033951 | 4/2004 |
| WO | WO 2007/063079 | 6/2007 |
| WO | WO 2008/090411 | 7/2008 |
| WO | WO 2010/063792 | 6/2010 |

OTHER PUBLICATIONS

International Search Report, as mailed on Feb. 9, 2010 in PCT Application No. PCT/EP2009/066309, 3 pages.

Written Opinion in corresponding International Application No. PCT/EP2009/066309, mailed Feb. 9, 2010.

U.S. Appl. No. 13/131,851, filed May 27, 2011 and its ongoing prosecution history, including without limitation Office Actions, Amendments, Remarks, and any other potentially relevant documents.

U.S. Appl. No. 13/151,235, filed Jun. 1, 2011 and its ongoing prosecution history, including without limitation Office Actions, Amendments, Remarks, and any other potentially relevant documents, filed Jun. 4, 2011, Bonadeo et al.

Machine Design, "Lasers Gauge Pitch", Machine Design, Penton Media, USA, vol. 67, No. 19, p. 40, Oct. 26, 1995.

* cited by examiner

SYSTEMS AND METHODS FOR MEASUREMENT OF GEOMETRICAL PARAMETERS OF THREADED JOINTS

CROSS-REFERENCE TO RELATED APPLICATIONS

This application claims priority to European Patent Application No. 10164636.2, entitled "METHOD FOR MEASUREMENT OF GEOMETRICAL PARAMETERS OF COATED THREADED JOINTS", filed Jun. 1, 2010, the entirety of which is hereby incorporated by reference and should be considered a part of this specification.

BACKGROUND

1. Field

Embodiments of the present disclosure relate to measurement of geometrical parameters of threaded connections and for assessing the quality of a coating deposition process. The disclosed embodiments are especially suited for threaded pipes used in the hydrocarbon industry and for similar threaded objects.

2. Description of the Related Art

Oil and gas pipe connections may be prepared with dry coatings in order to avoid the use of dopes and attendant drawbacks. For example, documents EP 1554518, EP 1954953, and EP 2102542, the entirety of each of which are incorporated by reference, disclose threaded joints where all or part of the threading is covered with dry coating.

Generally, dry coatings are applied after performing a threading operation of pipe ends. The dry coatings are designed to provide both high galling resistance during make up operations in the oil field and high corrosion resistance. Corrosion resistance is desirable during transport and storage of the pipes so as to inhibit damage to the pipes.

During manufacturing of threads in products such as screws, bolts, and threaded pipes, it is beneficial to verify that the geometrical dimensions of these pieces complies with tolerances set for the product. In addition, knowledge of the nature of the deviation from these tolerances can be used for feedback to the manufacturing process, allowing for the production of fewer products having geometrical dimensions outside of the tolerances.

A difficulty encountered in performing measurement operations on threaded products is the precision and repeatability of the measurements. In this particular technical field, several parameters are typically measured, such as taper of the pin and the box, the thread pitch, the thread height, the diameter of the pin or box, the pipe ovality, and run in and run out. In the past, there have been attempts to improve accuracy and repeatability of measurement operations and to fabricate measurement systems capable of measuring the thread shape of complex mechanical objects such as pipe threads used in the oil industry.

For example, U.S. Pat. No. 5,712,706 discloses a non-contact, laser-based sensor that is guided by a precision mechanical system. The system scans a thread profile and produces a set of computer images of the threading. The computer images are then analyzed to acquire quantitative information about characteristics of the threads, such as pitch, lead, root radius, flank angle, surface roughness, helix variation, and pitch diameter. However, U.S. Pat. No. 5,712,706 does not explicitly address explicitly the issue of piece misalignment. As a result, high precision is needed when aligning the piece to be measured with the mechanical system coordinates. This alignment can be conventionally achieved when the piece is at the threading machine.

Unfortunately, performing measurements at the threading machine has several disadvantages. In one aspect, performing measurements at the threading machine adds costly time to the threading process by inhibiting inspection and manufacturing from being performed at the same time. Instead, performing measurements at the threading machine entails placing delicate optics and precise mechanical components in a hostile environment (e.g., cutting oil and strong vibrations present). Further, when performing measurements at the threading machine the same mechanical movement that has to be verified is used, to some extent. Once the piece has been removed from the lathe, this alignment is very difficult to achieve manually. Consequently, the system disclosed by U.S. Pat. No. 5,712,706 only allows measurement of relative or local magnitudes (i.e. thread height by comparing contiguous crests and roots). Measurement errors introduced by a piece misalignment are not "noticed" according to U.S. Pat. No. 5,712,706, and in these cases produces an insufficiently precise measurement.

Furthermore, U.S. Pat. No. 5,712,706 does not address the measurement of thread parameters such as taper, run-in, run-out, black crest, length of complete thread. Specific process parameters, such as taper profile, pitch linearity, Fourier mode decomposition of ovality, lathe plate misalignment, hook end angle severity, are also not addressed.

In case where a coating is applied to the pipe threading (e.g., a dry lubricant), additional problems are encountered. As in the case of non-coated pipes, it is beneficial to ensure and verify the geometrical dimensions of the finished piece after the coating process so that tolerances set for the final product with the threading may be satisfied. In addition, the information on the nature of the deviation from these tolerances may be used as a feedback on the manufacturing process, allowing for the production of fewer products having geometrical dimensions outside of the tolerances.

Another difficulty encountered in performing measurement operations on coated joints is an inability to ensure that the coating material is not damaged during the measurement procedure (e.g., due to handling of the pipes and/or to the use of contact type measuring devices).

While measuring systems have been proposed for measuring coatings in general and measurement of coating applied on tubular products, none of these measurement systems is adapted to measurement of dry coatings applied on threaded parts of tubular joints.

In one example, a measurement technique employing ultrasound is known, however, it cannot be applied to coatings as thin as those applied in threaded joints for the hydrocarbon industry, since the wavelength of ultrasound is much larger than the thicknesses to be measured.

In another example, a measurement technique using eddy currents is known, however, this technique requires that the measurement device is placed either in contact or very close to the work piece. Because of the complex geometry and generation of boundary effects, it is difficult to use this technique on threaded parts of joints. The deformation of field lines because of the geometry and the fact that the sensor must be very near to the thread surface are two important constraints.

In a further example, a measurement technique based on X-ray fluorescence or back scattering is known where the coating highlights when it is irradiated and the fluorescence is reabsorbed by the coating. The amount of fluorescence measured is proportional to the thickness and the results are influenced by several factors. It is not a technique generally applicable and, in complex cases, the results depend on the angle of incidence of X-rays. Another drawback is the use of X-rays which are harmful to operators.

In an additional example, a measurement technique based on infrared (IR) absorption is known, where excitation of the coating is made by visible light. The application of this technique depends upon whether the coating is made of a material which is excitable by light and upon the grade of IR absorption.

Therefore, a need exists for measurement devices and methods that provide measurement of threaded products that are repeatable, satisfactory, and precise manner.

SUMMARY

An object of the present invention is to provide a measurement method which overcomes the drawbacks and limitations described herein.

An object of the embodiments of the present disclosure is to provide a method for accurate, non-contact inspection of threaded objects. In certain embodiments, the method may be performed automatically. In further embodiments, the method may be suitable for threads of pipes employed in oil exploration, especially of pins and boxes.

In accordance with one embodiment, a method of measuring thread parameters of a threaded object coated by at least one layer of coating material is provided. The method comprises obtaining a shape of the threaded object including a nose, identifying a first spatial reference system for the threaded object comprising first co-ordinate axes X', Y', Z', and identifying a first spatial reference system for the threaded object comprising first co-ordinate axes X', Y', Z'. The method also comprises, determining at least one trajectory on the threaded object in the second spatial reference system, the trajectory including selected measurement points, and obtaining first position data for the threaded object at the predefined measurement points of the at least one trajectory in the second spatial reference system. The method also comprises converting the first position data for the threaded object from the second spatial reference system to the first spatial reference system to yield first measurement results, coating at least a portion of the threaded object with a selected coating, and obtaining second position data for the coated, threaded object at the predefined measurement points of the at least one trajectory in the second spatial reference system. The method also comprises converting the second position data for the coated, threaded object from the second spatial reference system to the first spatial reference system to yield second measurement results, and determining the thickness of the coating from a comparison of the first and second measurement results.

In accordance with another embodiment, a measurement device is provided. The measurement device comprises one or more optical sensors configured to measure positions of a surface of a threaded object, and a moveable mount configured to hold the one or more optical sensors. The measurement device also comprises a computing device configured to synchronize output signals from the one or more optical sensors with spatial positions of the one or more optical sensors. The computing device is also configured to calculate a transformation matrix, relating a first spatial reference of the threaded object to a second spatial reference system defined by the one or more sensors for defining the relative position of the threaded object with respect to the second spatial reference system.

BRIEF DESCRIPTION OF THE DRAWINGS

The foregoing aspects and many of the attendant advantages will become more readily appreciated as the same become better understood by reference to the following detailed description, when taken in conjunction with the accompanying drawings.

DETAILED DESCRIPTION

The terms "approximately," "about," and "substantially" as used herein represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of the stated amount.

In the disclosed embodiments, reference is made to a pin of an oil or gas pipe. However it may be understood that embodiments of the disclosure may be applied to any other similar threaded objects, such as screws or similar objects. All these kinds of objects, at a certain stage of the measurement method, may be coated, using any type of coating technology. In certain embodiments, the coating may be a dry coating but, in alternative embodiments, other types of materials may be used as coatings, depending on the function to be achieved by the coating. The coating is not shown nor indicated in the figures because of their schematic character and of the small thickness of the coating layers. However, it may be further understood that the figures apply also to the cases where a coating is present on the measured object.

Figure 1:
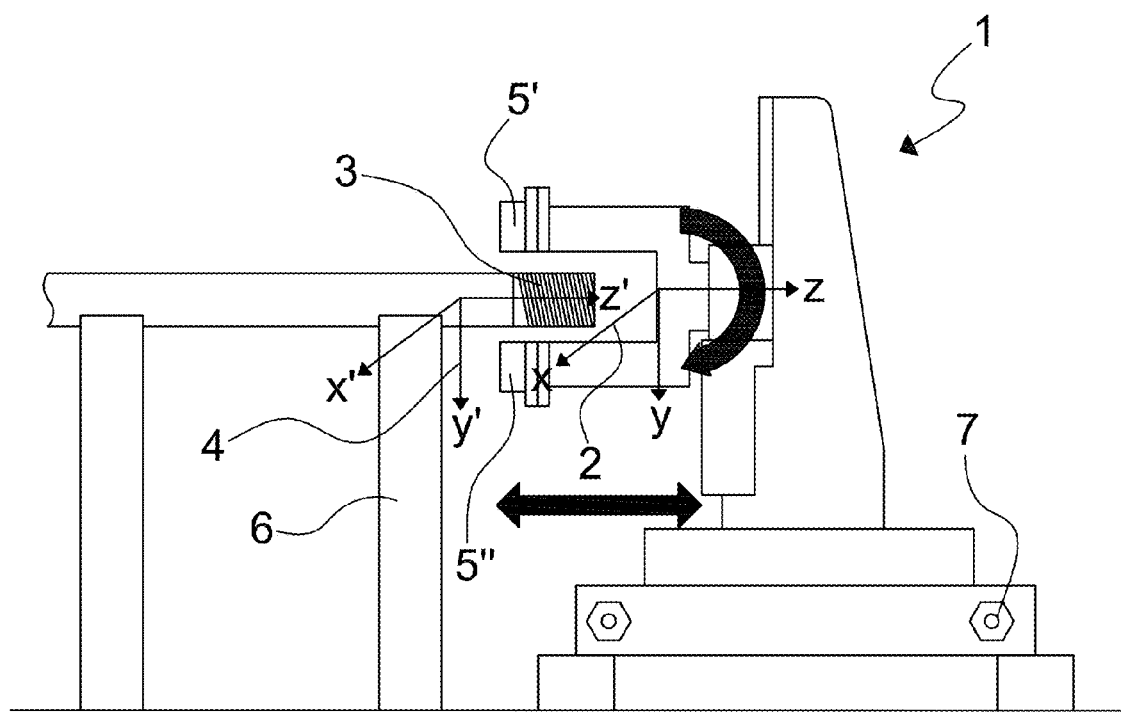
FIG. 1 is a schematic, axonometric view of a measurement device for measuring the location of a surface of a threaded object with respect to a sensor.
Figure 1A:
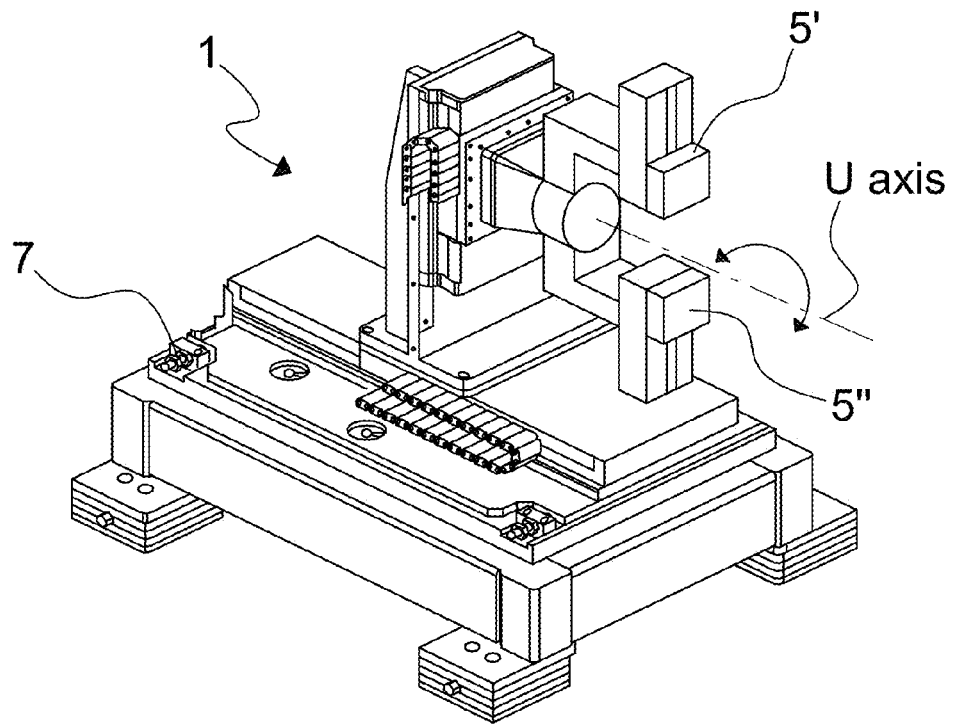
FIG. 1a is a schematic, perspective view of the measurement device of FIG. 1.

With reference to FIGS. 1 and 1a, a schematic illustration a measurement device 1 is shown. In certain embodiments, the measurement device may be an automatic thread inspection optical system based on laser displacement sensors. The measurement system 1 may have its own Cartesian reference system 2 that is defined by the orthogonal axes X, Y, Z. A threaded portion of a pin 3 to be measured is shown on the left of FIG. 1. This pin 3 may have its own Cartesian reference system 4 that is defined by the orthogonal axes X', Y', Z'. In FIG. 1, the pin 3 is positioned far from the measurement device 1 and in a rest position (e.g., on a bench 6).

When initial installation of the measurement device 1 is performed, the pin 3 may be mounted on the measurement device 1 to perform the measurement operations according to the embodiments of the measurement procedure discussed below. For example, the respective pin 3 and measurement device 1 reference systems are placed as close as technically possible one to each other using the horizontal, vertical angular, and lateral displacement movements provided by the device (see FIG. 1). Nevertheless, the two reference systems may not coincide exactly and small misalignments, both in the angular position and in the lateral position of the reference system 2 of the pipe, with respect to the measurement device may still exist. Even more, when a different pin 3 is mounted on the measurement device 1, the angular position and the lateral position of the new pin will differ from the previous pin due to placement errors and geometrical differences (such as hook end) between the two pins. Due to these reasons, under operative conditions the misalignment of pins, or more generally of the threaded parts of pipes, with respect to the measurement device, is approximately on the order of millimetres in the linear displacement and approximately on the order of a degree in the angular displacement. Only by adjusting the position of every pin a smaller misalignment value could be achieved. However, that scenario is impractical in reality. Embodiments of the present disclosure enable the measurement device 1 to work without any lateral or vertical adjustment of the knobs 7, which are shown in FIGS. 1 and 1a, after initial installation.

The measurement device 1 may include a plurality of laser sensors. For example, two laser displacement sensors (e.g., displacement sensors 5' and 5") may be mounted on a yoke piece. In certain embodiments, the yoke piece may be machined from a single aluminium piece in order to minimize mechanical movements. This piece or head may be mounted on a rotational stage that is configured to pivot about a U-axis, and belongs to the head of the measurement device, together with the laser sensors 5' and 5".

Each sensor 5', 5" may be mounted on an X stage that can be moved in the radial direction (i.e. the X-axis) by use of linear rotary motors. Angular and linear movements of these stages parallel to the Y axis and orthogonal to the X axis may allow the stage to be approximately aligned along the same line. Both laser sensors 5' and 5" can also be adjusted by lateral and angular displacements to align the center of the laser emission with respect to the center of rotation of the measurement device 1.

In further embodiments, the stage X in addition may be motorized so as to allow an automatic change of product diameter while maintaining the sensors within their range.

The measurement device may further include a linear stage, (moving along the Z-axis) that allows displacement of the head parallel to the device axis Z. The linear stage, movable along the Z axis, may be mounted on a base that is hard coated on the bottom to allow smooth displacement with respect to the base when the measurement device 1 is set up for the first time, as shown in FIG. 1a. Four knobs, e.g. placed one on each corner, may allow for horizontal angular and lateral displacement of the measurement device 1 in a plane. There are provided screws, or equivalent mechanisms, to fix the measurement device 1 in place and to inhibit movement of the device 1 once the initial alignment has been accomplished. There is further provided, advantageously, a wedged pad on each of the four legs to regulate height and out-of-plane angular alignment. With the ability to adjust the angular and lateral displacement of the measuring device 1, the measuring device may be easily installed in a plant, allowing for small corrections to levelling tolerances, to conveyer alignment and to imperfections in the levelling of the plant floor.

The manner in which embodiments of this measurement device may be used to perform measurements on threaded objects are described hereafter. After the initial installation is carried out, as described above, measurement operations may comprise at least two operations: data acquisition and data analysis.

The data acquisition operation is now described. During this operation, the laser sensor may output signals and positions of servos that are stored. The signals may be stored in a data storage device in communication with the measurement device 1 in a synchronized manner, ensured by the use of hardware signals to enable windows and counters. Embodiments of the data storage device may include, but are not limited to, network-based storage capable of communicating with any component of the measurement device 1 via a network 112 and include storage devices that are in local communication with any component of the measurement device 1.

The signals used are described in greater detail below.

Figure 2:
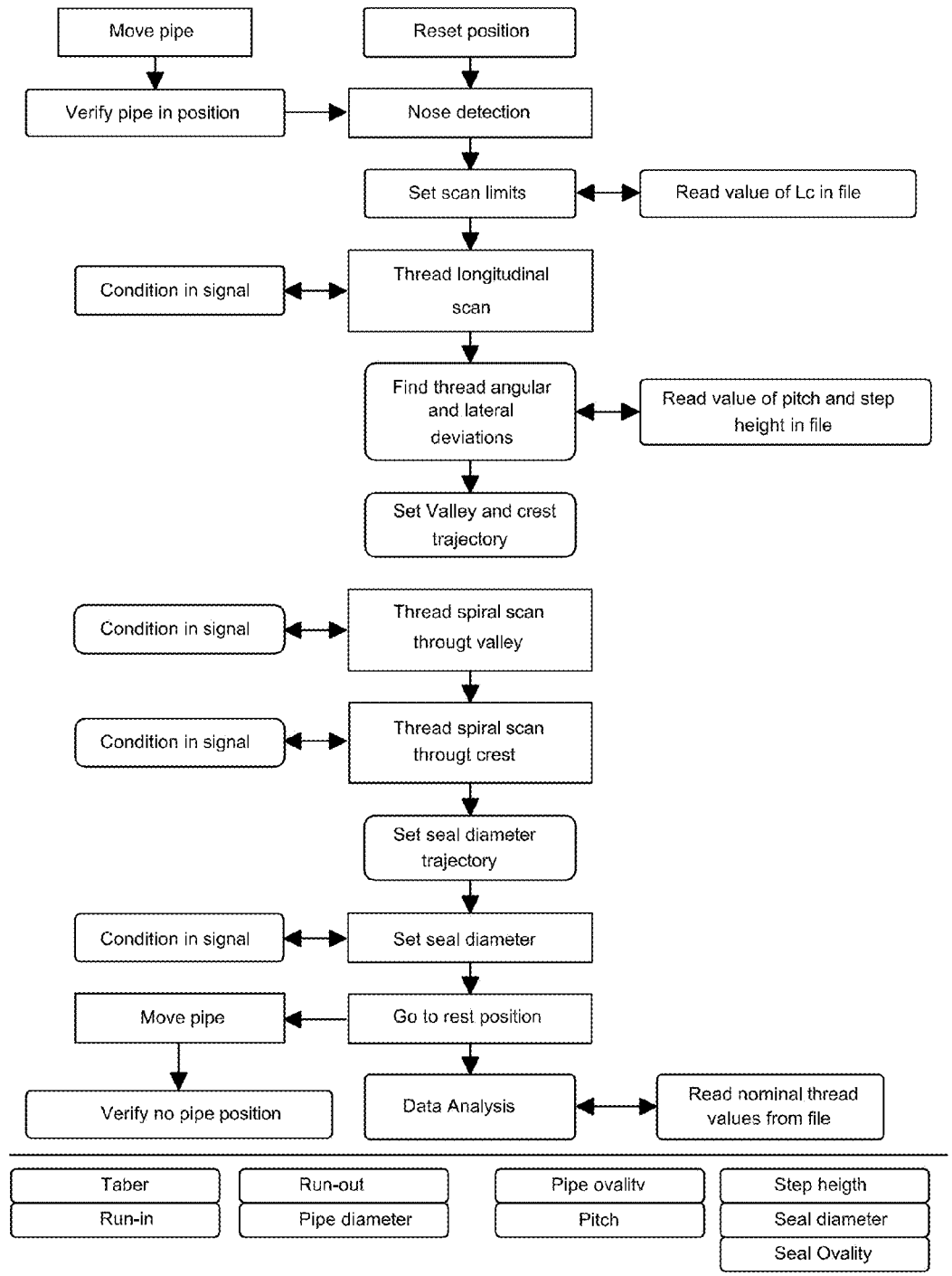
FIG. 2 is a flow diagram illustrating non-limiting operations of embodiments of the disclosed measurement method.

FIG. 2 is an embodiment of a flow diagram 2 illustrating the data acquisition operations governing the measurement process once the initial calibration and plant installation has been performed. The flow diagram of FIG. 2 begins with moving a pipe and verifying that the pipe is in position aligned to the measurement device. The measurement device may further execute a first longitudinal scanning operation along the threaded portion of the pipe to find the relative position of the pipe nose with respect to the frame of reference of the measurement device. After the relative position of the nose is detected, all distances reported during measurement may be referred to that point. If the measurement operation of the threaded pipe provides for only one scanning operation, the data may be gathered only in correspondence with points belonging to the path followed by the sensors 5' and 5". This is generally done because the data collected are considered sufficient to the needs of the users.

If the measurement procedure on the threaded object provides for several scanning operations along several trajectories on the coated or uncoated surface of the threaded portion of the threaded object, data may also be collected on predefined points along these trajectories. The choice of the measurement points where data are gathered may be made in such a manner that a matrix that describes the quadratic form has maximum rank when values corresponding to these points are inserted in it.

In an embodiment of the disclosed method, a plurality of longitudinal profiles, e.g. six, may be scanned. In certain embodiments, the scan may be performed at equally spaced angular steps. Data gathered by these scans may be processed to remove spurious peaks and pass encoder counts to physical units. The data may be further used to calculate a first estimation of the thread angular misalignment with respect to the frame of reference of the measurement device 1. The nose position may be reassigned by averaging the six nose positions corresponding to the six scans.

These scanning operations may also used to detect the positions of the crests and roots of the threads of the threaded object. By interpolating this information, a spiral trajectory table may be determined that enables successive scanning operations over the center of the crests or roots of the thread. Data acquired by those spiral scanning operations may also be conditioned and used to measure more precisely the misalignment in respect of the thread frame of reference. After this operation, and having detected the orientation of the thread, a table for the seal or seals, run in and run out trajectories, can be constructed in the reference frame of the piece (X',Y',Z') and transformed to the device coordinate system and executed.

After the scanning operations are completed, the head of the measurement device may return to its rest position. Subsequently, data analysis may begin in order to determine desired parameters of the thread under test.

The pin 3 may be then dismounted from the measurement device 1 and a coating operation of the threaded object may be performed in an appropriate place. One or more layers of coating material are laid on at least part of the pin threading and/or surface. The coating can be made also on specific surfaces of the threading, like thread crests, flanks or roots by means of any known technology.

When the coating operation is performed, the pin 3 may be again mounted on the measurement device 1 or a similar device. The measurement steps described above may then be replicated on the same predefined trajectories on the surface of the threaded portion of the threaded object. Data may again be collected on the same predefined points along these trajectories, which were selected before the coating operation, and the same calculations, as described above, may again be performed. A comparison of the data acquired before coating and after coating of the threaded object may be carried out and, in this manner, the thickness of the coating at all measurement points of the pin 3 may be calculated.

The above described procedure is now described in detail, where various embodiments of the measurement procedure are disclosed. This measurement procedure applies to both before the pin 3 is coated and after the pin 3 has is coated. It can be appreciated that embodiments of the measurement method can be applied to the cases where coating is made in successive distinct layers, to measure the quality of the intermediate layers and of the final layer resulting from the superposition of various layers.

Following movement and verification that the pipe is in position, nose detection may be performed. Nose detection may include executing a linear scan along the Z-axis between two reference distances where the nose of the threaded object is estimated to be located. It will be appreciated that, in certain embodiments, this linear scan may be the only scanning operation predefined in the measurement method. In alternative embodiments, the linear scan may be the first scanning operation of a plurality of successive scanning operations.

Signals provided by the laser sensors 5 may be further analysed by making a check of the presence or absence of Out Of Range (OOR) values. An OOR value is a non-valid point (i.e. out of the physical range of the sensor) that is sent by a sensor when no object is found in the measurement range of the sensors. These signals may be processed by selecting a sampling window including a selected number of data points (e.g. fifty data points) and verifying that all samples are not OOR. The number of data points may depend on several factors. Examples of these factors may include, but are not limited to, the shape of the pin surface, the type of threading, the type of joint, etc. In an embodiment, the number of selected data points may be above or below fifty.

The sampling window may be moved one step further and the values of the signals sent may be checked again until all samples in that window are recognized as valid data points after processing. The first sample may be the nose position of the pin.

Figure 3:
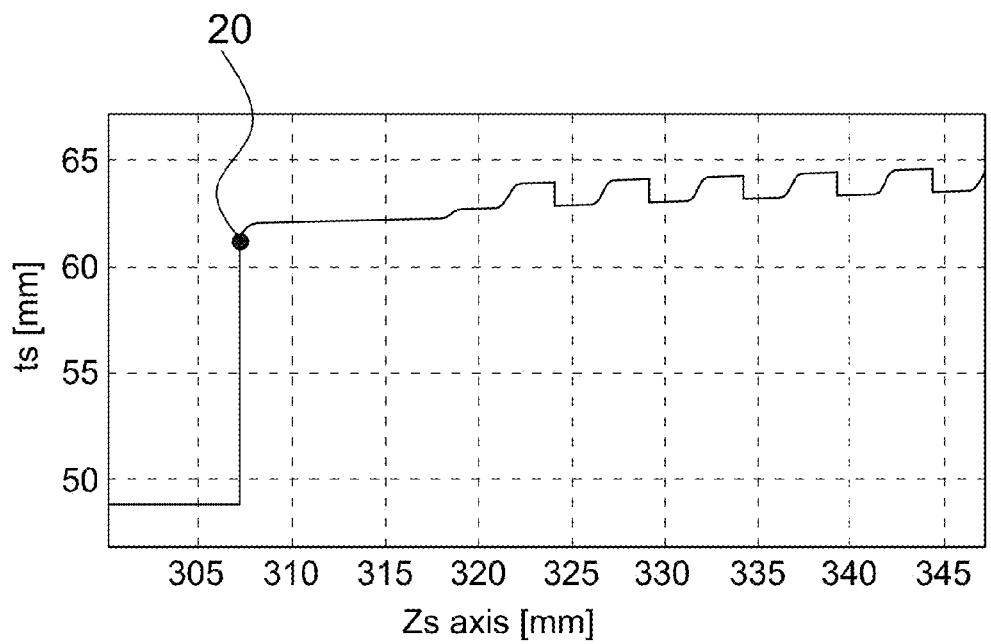
FIG. 3 is a graph illustrating data acquired in an operation of an embodiment of the disclosed measurement procedure.

The graph of FIG. 3 illustrates the results produced by a scan during nose detection. OOR values are shown previous to the encounter of the laser sensors with the pipe nose. For example, the dot 20 indicates the position, with respect to the Z axis, where the nose has been detected. After the nose position has been detected, scanning is stopped, and the data acquisition procedure may be started.

In certain embodiments, an accurate determination of the nose position is optional for measuring most of the thread parameters of interest that are based on relative distance measurements. Exceptions may include measurements of pipe and seal diameters. These parameters may be measured at a precise distances relative to the nose position as the thread taper changes its value if measured elsewhere.

Figure 3A:
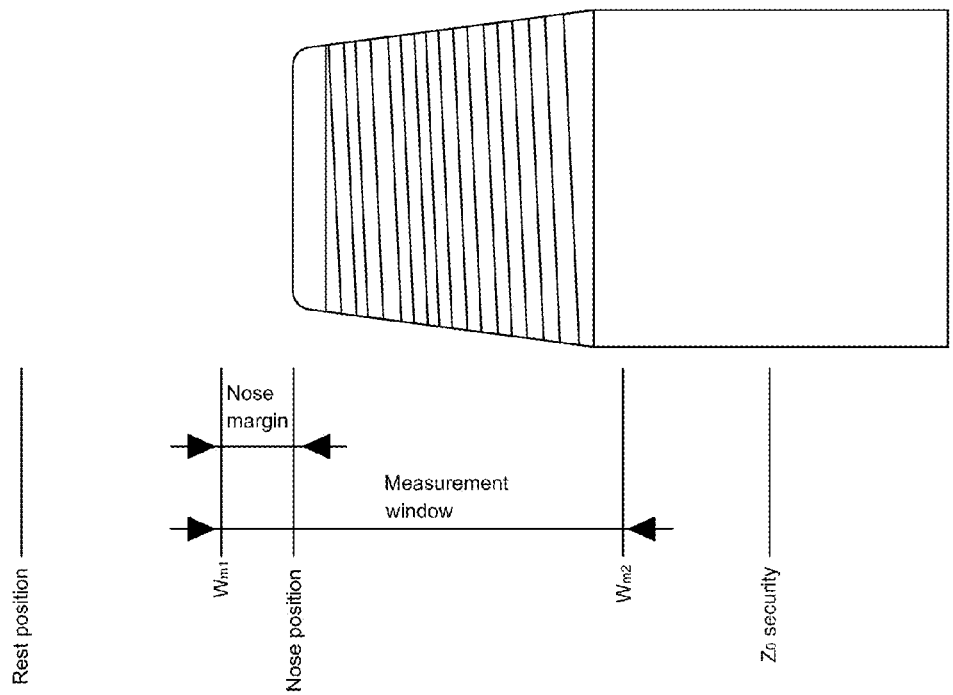
FIG. 3a is a schematic illustration of detail of a coated threaded object on which an embodiment of the disclosed measurement method is performed.
Figure 4:
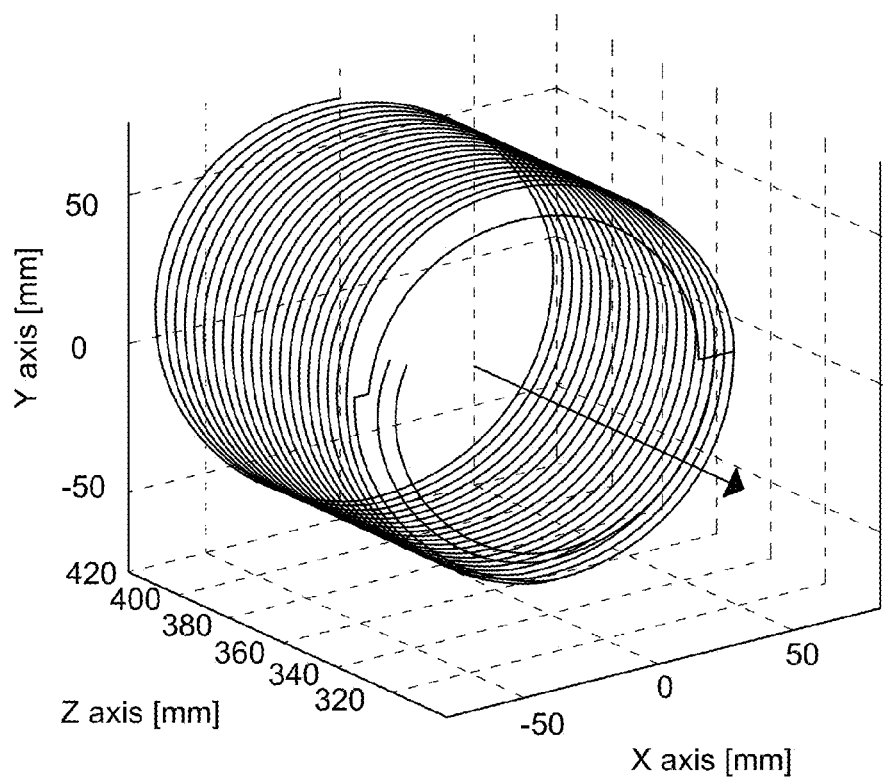
FIG. 4 is a graph illustrating data acquired in a further operation of an embodiment of the disclosed measurement procedure.

In cases where nose detection is necessary, several longitudinal scanning operations may be performed along the Z-axis direction. In certain embodiments, 3 scans may be performed, however, greater or smaller numbers of scans may also be performed, as necessary. The scans may be conducted by acquiring outputs from both laser sensors 5', 5" at the same time. The limits of the scanning range window are represented generically in FIG. 3a.

From its resting position, the head of the measurement device 1 may be driven back to the first position of the measurement window. This first position corresponds to the nose position, which is at the end of the nose margin and is indicated by $W_{m1}$.

When the sensors are placed in position $W_{m1}$, a movement towards security point $Z_0$ is indicated and the window signal that resets encoder counts is enabled. The number of encoder counts to be acquired by the laser sensors 5', 5" may be preset to fit into the measurement window longitude. When this preset number is reached, the head of the measurement device 1 is commanded to stop at the point indicated by $W_{m2}$. In this manner, the measurements from the laser sensors 5', 5", together with encoder counts, may be acquired in the measurement window segment. Longitudinal scans may be subsequently implemented in the inverse direction. Similar limits for encoder counts to be acquired by the laser sensors may be set also for these movements in the opposite direction. This movement in the reverse direction towards the rest position starts from point $W_{m2}$ and ends in point $W_{m1}$, where the head of the measurement device 1 stops after having reached the number of predetermined encoder counts to fit the measurement window.

Figure 6:
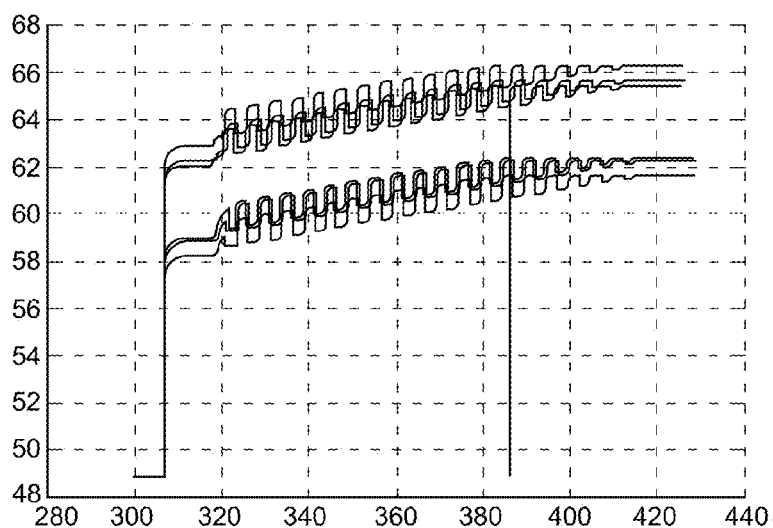
FIG. 6 is a graph illustrating results of additional operations of an embodiment of the disclosed measurement procedure.

FIG. 6 shows a typical longitudinal scan, where signals generated by both laser sensors 5', 5" (placed at an angular distance of 180° apart) are acquired. In this example, the three scans result in six profiles (i.e. two groups of three profiles), where each scan corresponds to one of the laser sensors 5' and 5" of the thread under test. These scans are useful for providing a first estimation of the misalignment of the threads of the threaded object. If necessary, the measurement device 1 may be operated with only one of the two laser sensors 5', 5" generating signals.

The quantity of scans, illustrated herein by way of example, can also be more or less than three, depending on the threaded object being measured and the thread parameters that are sought. In the examples discussed herein, pitch and step height along six generatrices are the parameters sought.

Alternative embodiments of the measurement method provide data acquisition operations for detecting selected points on thread crests and roots. These data acquisition operations may be conducted by performing a selected number of longitudinal scans parallel to the Z-axis. Data collected from these scans may also enable points to be determined on thread roots and crests for use in identifying trajectories along which two subsequent spiral scanning operations are performed. The spiral scanning operations may be conducted along the thread crest and along the thread root. By being generated previously in this manner, the trajectory may be configured so as to avoid falling off the crest or climbing out of the root during the scanning operation when the object is misaligned with respect to the X', Y', Z' co-ordinate system of the pin 3.

The measurement operation may start by detecting thread load flanks. This detection may include detecting load flanks for each longitudinal profile and may be performed by differentiating the whole data vector and evaluating values that override a preset threshold. A vector containing all zero values may be generated, excluding those detected points which are candidates for indicating the presence of a load flank.

Figure 5:
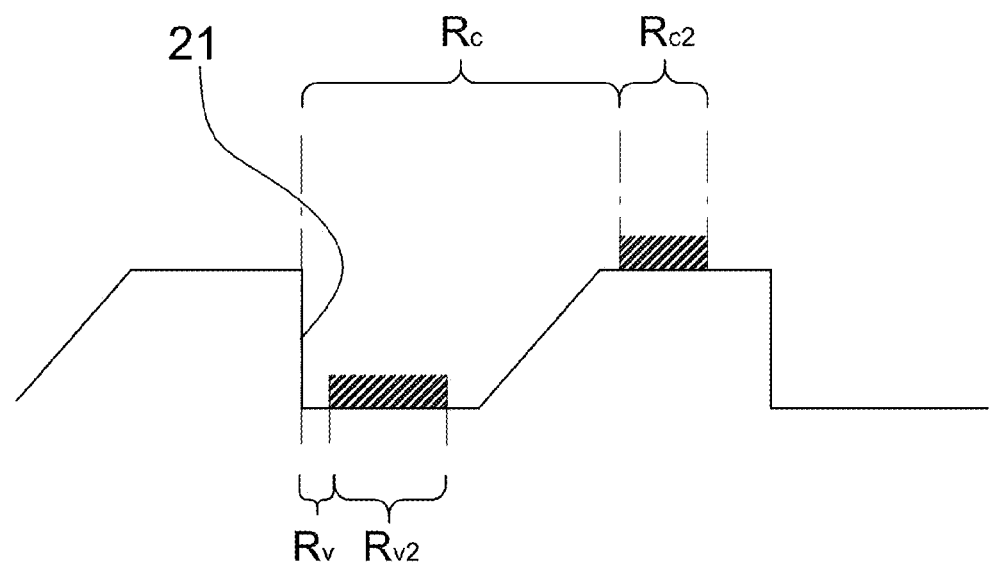
FIG. 5 is a schematic illustration of a longitudinal section of a thread where measurements are made.

Another vector may be generated which represents a theoretical comb with teeth of a specific detection width and nominal pitch separation between the teeth. These two vectors may be cross correlated in order to find the relative position between the comb and the load flank 21 candidate vector that maximizes the cross-correlation (FIG. 5). The cross-correlation may include performing a scalar multiplication of the two vectors and finding the sum of the resulting vector while changing their relative vector index.

Subsequently, load flanks 21 may be assigned in correspondence with the points found as candidates for each comb tooth according to the following criteria:

If one candidate flank is present (referred to as type 0): this flank is a real load flank.

If no candidate flank is present (type 1): a flank is created just in the middle of the thread comb interval for the purpose of producing the spiral trajectory.

If more than one candidate flank is present (type 2): there are spurious flanks in the thread comb, so the nearest to the middle point of the thread comb interval is determined as the real load flank. The remaining flanks are dismissed.

If an out of range is found in the interval (type 3): the flank is discarded and a virtual flank is created for the purpose of producing the spiral trajectory.

Figure 7:
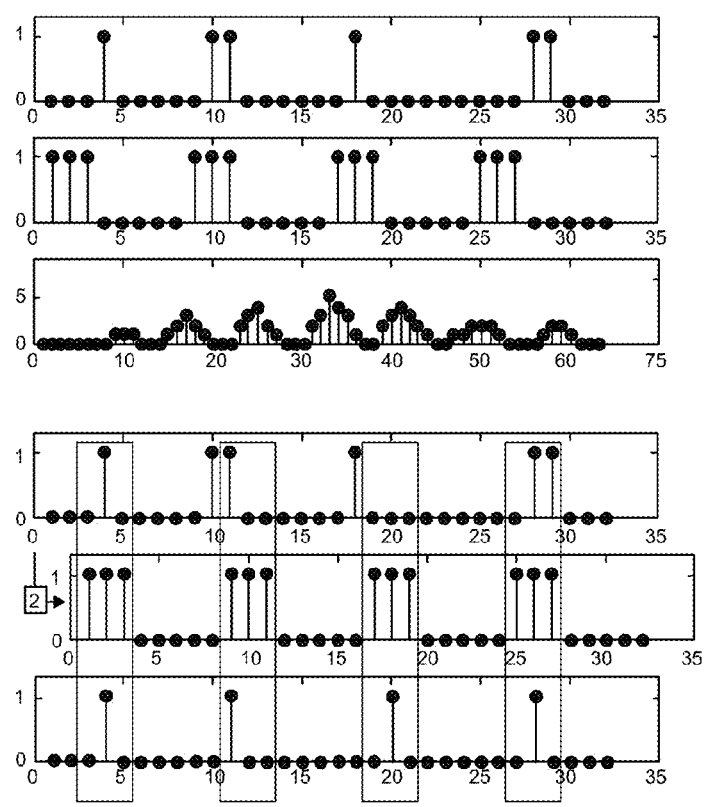
FIGS. 7a-7f are graphs illustrating hypothetical assignations of load flanks.

FIG. 7 shows hypothetical load flank candidates and comb vectors in the three mentioned cases possible for assigning loading flanks.

Another embodiment of the measurement method provides for assigning points along crests and roots. The crests and roots segments may be determined following the thread mechanical drawings with the parameters $R_c$, $R_{c2}$, $R_v$ and $R_{v2}$ as illustrated in FIG. 5.

Each segment may be conditioned. Conditioning may include filtering OOR and possible peaks, taking into consideration that the segment is assumed to be a line. Then, the point corresponding to either root or crest is calculated as the mid segment point.

FIG. 7 illustrates of a longitudinal scan where those points detected as being root and crest points are indicated. Graph (a) shows the candidates for load flanks, graph (b) shows the theoretical comb, graph (c) shows the cross-correlation, graph (d) shows candidates for load flanks, graph (e) shows the displaced theoretical comb, and graph (f) shows assigned load flanks. As can be seen in FIG. 7, points may be generated by extrapolating the determined points in the threaded portion for location prior to the nose position, and after the end of the thread where the non-machined part of the pipe starts. This may be done to smoothly enter and emerge from the threaded portion during execution of the spiral scan, to obtain the phase of the thread relative to the measuring device frame of reference, to estimate the position of the black crest, to calculate the lathe eccentricity axis, and to measure the pipe hook end.

The root points determined in each longitudinal scanning operation may also be used for fitting a quadric surface representing the cone of the thread being analysed. This fitting is performed to determine a first estimation of the thread angular misalignment with respect to the reference frame of the measurement device 1. Crest points are preferably not used in this calculation for two main reasons:

a) The determination of crest points is more inaccurate than that of root points. For example, the portion of the pin where determination of the roots is performed is longer.

b) The number of root points over the thread surface cone is higher than that the number of crest points due to the presence of "black threads" generated in the manufacturing process.

The generic matricial form of the quadric surface is described in Formula [1].

$$\bar{x}^t.A.\bar{x}+\bar{b}.\bar{x}=1 \qquad [1]$$

where $\bar{x}=[x, y, z]^t$ is a point of the quadric in the 3D space, A is a symmetric matrix related to the quadric (it is formed by nine parameters, three for translation, three for orientation and three for the quadric form as expressed in a canonic frame) and $\bar{b}$ is the quadric displacement vector.

The selected data may be fitted to the expression shown in Formula [1] by using a least squares approximation. From this fitting, the parameters of the quadric. (e.g. the parameters that conform to A and $\bar{b}$) may be obtained.

These data may be useful for the conformation of a linear transformation and its inverse transformation between the measurement device 1 and thread reference frames.

Spiral scannings may be further performed, along both root and crest of threads. The information acquired before relating to the root and crest mid point positions, for each longitudinal scan, may be interpolated and used to build two spiral scanning tables. In certain embodiments, all of the root mid points may be transformed to the thread coordinate frame. Afterwards, a linear fit may be performed over the data resulting from a t vs. Z arrangement Subsequently, a new set of points may be generated segmenting the fitted line with a regular step. These points may be transformed back to the reference frame of the measurement device 1 and passed to a controller for the calculation of the servo references. The same procedure may be applied on the crest mid points for generating the crest scanning table.

The root scan may be executed starting from the nose while the crest scanning may be executed in the opposite direction, considering the Z-axis. FIG. 5 shows a typical root and crest scanning expressed in respect of the reference frame of the measurement device 1. Data obtained from the root spiral scan may be used to calculate a better estimation of the measurement device 1 to thread misalignment that is also used to recalculate the transformations between reference frames that are applied in the data analysis.

Figure 8:
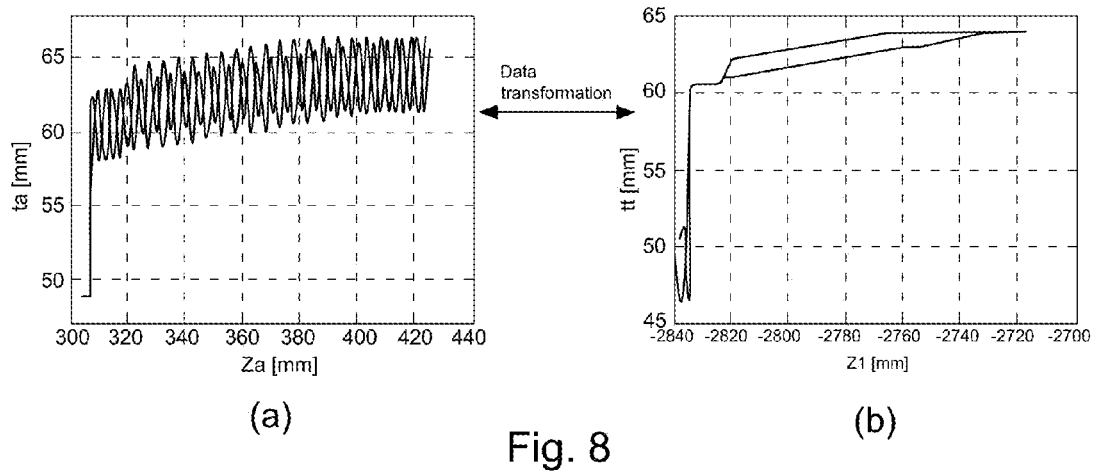
FIGS. 8a-8b are graphs illustrating results of spiral scans.

FIG. 8 illustrates the t vs. Z graphs for the reference frame of the measurement device 1. Graph (a), illustrates the t vs. Z graph as data are acquired and for the thread reference frame, Graph (b) illustrates the t vs. Z graph transformed using the misalignment estimation calculated from the spiral scans. The graph (a) of FIG. 8 shows on the left what the effects of misalignment are on the acquisition procedure.

Figure 9:
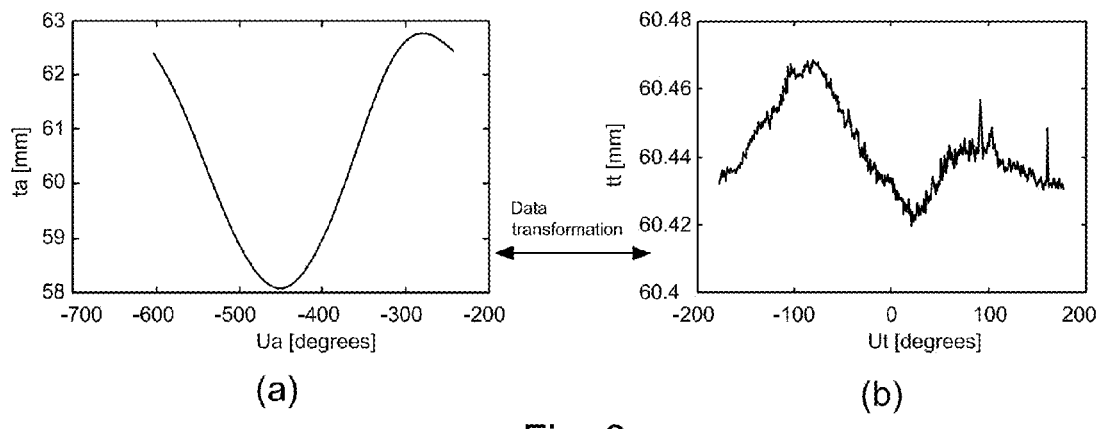
FIGS. 9a-9b are graphs illustrating results of seal scans.

In an embodiment of the measurement method, a data acquisition procedure is provided for scanning the seal of the thread. In this case, an ideal circular trajectory is generated with reference to the thread reference frame at a predetermined distance from the nose. The thread reference frame may be further transformed to the reference frame of the measurement device 1 for its execution. FIG. 9 illustrates two graphs containing the results of a typical seal scan. Graph (a) illustrates the scan expressed in the measurement device reference frame. Graph (b) illustrates the scan in the thread reference frame.

In certain embodiments, it may be necessary for this scanning trajectory to be executed starting at a predefined distance from the pin nose and in alignment with the threaded object. For example, the nose profile may be complex and the radius measured may be highly dependent on the exact position measured. A good estimation of the nose position may be calculated when a plurality of scans is made (e.g. six scans). In this example, the nose position detected on each of the six longitudinal scans may be retrieved. These data may then be transformed to the thread reference frame and averaged to obtain a single, more accurate, nose reference.

In another embodiment of the measuring method, the phase of the thread with respect to the device reference frame may be retrieved from the spiral root scan and a longitudinal trajectory may be set in the thread reference frame such that it passes through the measuring points determined in the inspection report for the measurement of the run-in. Similarly, a trajectory may be set for the points defined for the measurement of the run-out.

After data acquisition operations are completed, data analysis may be performed on the acquired data, but transformed to the thread reference frame, as a final part of the measurement method according to the invention. Unless otherwise indicated, the data discussed herein are expressed in terms of the threaded object reference frame.

Figure 10:
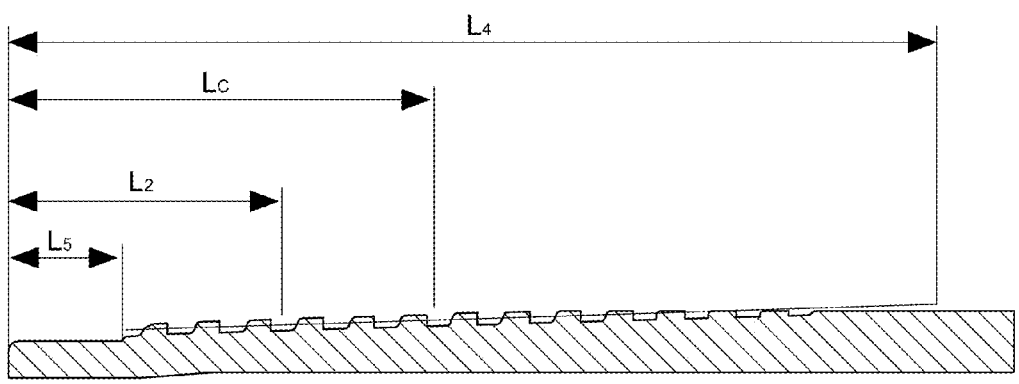
FIG. 10 is a schematic illustration of a scheme of the threading on which an embodiment of the disclosed measurement procedure is used.

Most of the parameters are indicated in relation to different length references taken on the thread and referenced to the nose position. FIG. 10 illustrates three references that may be used in data analysis and that will be referred to below.

$L_5$ is the length to the beginning of the thread.

$L_2$ is the reference length for the thread diameter and ovality calculation.

$L_c$ is the minimum length where the thread parameters must fulfil the tolerances.

$L_4$ is the length to the end of roots and crests, which is lower than the pull-out length where the run-out is measured.

One operation of data analysis is determination of the taper. The outer surface of the cone thread may be described by Equation [2]:

$$t_{thread} = (R_0 - A \bullet Z_{thread}) \quad [2]$$

where $t_{thread}$ and $Z_{thread}$ are the radial and azimuth coordinates in the thread frame of reference, $R_0$ is the primitive radius, and A is the taper of the pin threading.

Figure 11:
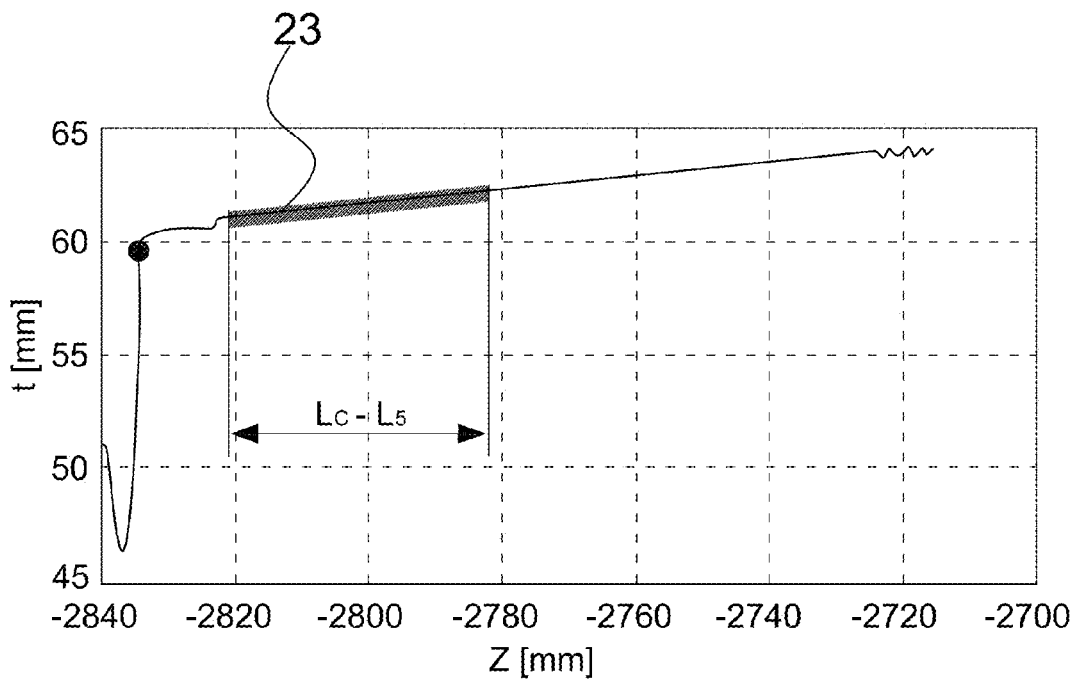
FIG. 11 is a graph illustrating results of thread root scans.

To calculate the taper, the t vs. Z relationship from the root scan of the thread may be used. Data acquired previously between $L_5$ and $L_c$, corresponding to segment 23 of the curve, may be analyzed, as illustrated in FIG. 11. A linear fit may be performed over these data 23 to calculate the slope, comprising the values of taper and of A. The deviations of the data with respect to that linear fit may be calculated. Those deviations contain information regarding the machining process (e.g. the non-compensated forces due to the change in pipe stiffness along the thread object and the over tightening of the pipe on the lathe). This information can be retrieved using a Fourier modal analysis as a function of the thread position.

For example, a large three-mode may indicate over tightening of the pipe on the lathe, while a parabolic behaviour of the fundamental mode may indicate that the tool was taken before the end of the $L_c$.

Figure 12:
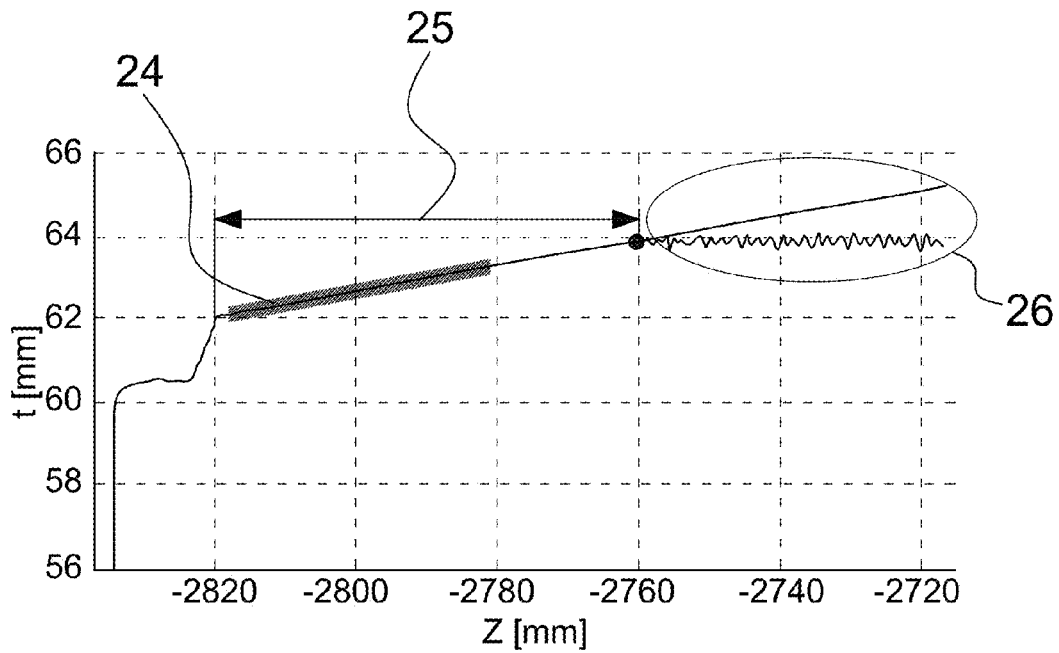
FIG. 12 is a graph illustrating results of thread crest scans.

Full thread length, corresponding to the segment 25 of the curve of FIG. 12, may be analysed considering the data gathered from the crest scanning. A linear fit may be performed using the acquired, filtered, data between $L_5$ and $L_c$, corresponding to segment 24. Deviations of the data with respect to the linear fit may be calculated. Subsequently those values of $L_5$ that are more than about 0.1 mm greater than this linear fitting may be identified, corresponding to segment 26 of the curve in FIG. 12.

With these values, a new linear fit (using the Z positions and the errors) may be performed and the zero abscissa may be calculated. This value may be set as the upper limit for the full thread length, as illustrated in FIG. 12.

Further analysis can be performed using the non-machined part of the pipe, illustrated in FIG. 12. These values may correspond to the pipe with a "virgin" surface and can provide information on the position of the thread with respect to the pipe at the moment of machining the part. For example, if the lathe has a misaligned plate, the thread may be off-axis with respect to the pipe. In another example, if the pipe has a hook end, the pipe and thread axis may not be parallel. Those variables can be easily calculated by finding the transformation between the pipe and thread coordinate systems.

Another data analysis operation according to embodiments of the disclosed measurement method may relate to calculation of thread diameter and ovality. Thread diameter and ovality may be evaluated in two ways using the root spiral scan. The data being analyzed may be those comprised in the zone corresponding to $L_2 \pm 2$ thread pitches. Root points defined in this zone (FIG. 13(a) showing the thread lateral view in section), may be linearly fit, after which this fit linear function may be evaluated to obtain the radius.

Alternatively, root points for each radius determination may be performed on generatrices. In certain embodiments, the generatrices may be equally spaced at angular distances 27. In further embodiments, the generatrices may be equally spaced at angular distances 27 of three degrees. On each generatrix, data for each root may be averaged considering a generatrix width 29 of typically, but not necessarily, 5 degrees (FIG. 13(b) illustrating a thread top view). This implementation is similar to the mill procedure used with the MRP gauge.

Figure 13:
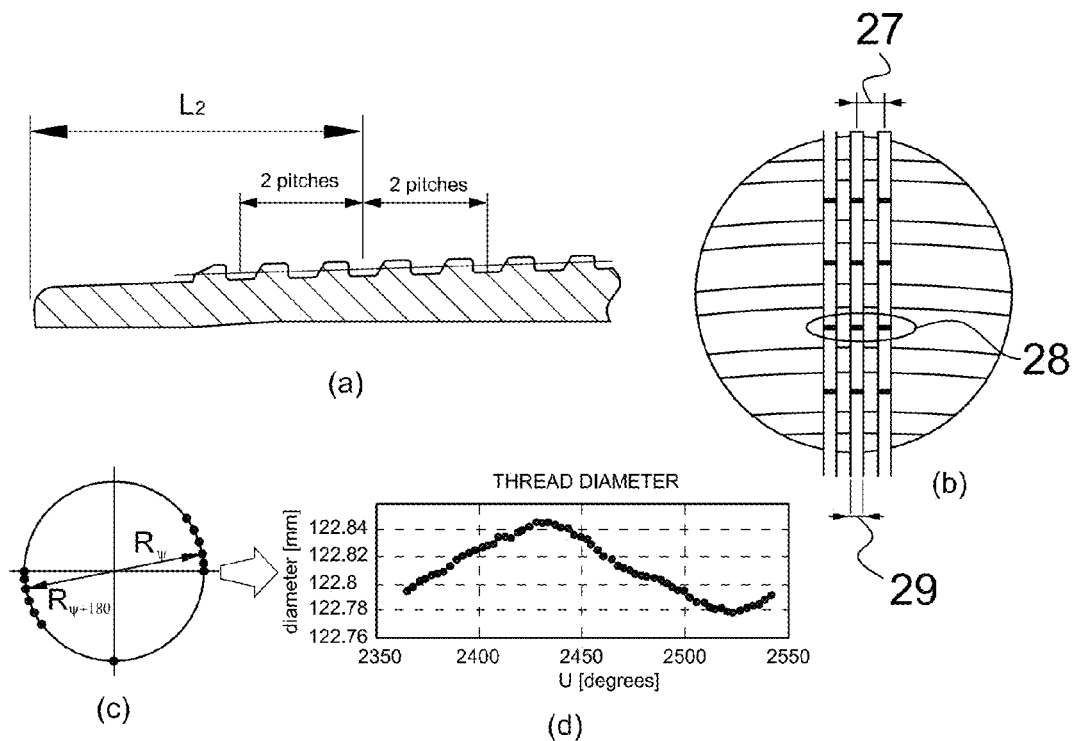
FIGS. 13a-13d illustrate threading schemes on which embodiments of the disclosed measurement procedure is used.

Radii of defined points (circle 28 of FIG. 13(b)), may be calculated for generatrices varying within the range between about 0 to 180 degrees. In certain embodiments, steps of 3° may be employed, together with the opposite generatrices for diameter calculation, as shown in FIG. 13(c), illustrates a thread frontal view. Successively thread diameter and ovality may be calculated using Equations [3] and [4]:

$$\text{Diameter} = (D_{max} + D_{min})/2 \quad [3]$$

$$\text{Ovality} = (D_{max} - D_{min})/2 \quad [4]$$

where $D_{max}$ and $D_{min}$ are the maximum and minimum diameters calculated through this process, respectively. The results are shown in the FIG. 13(d).

Figure 14:
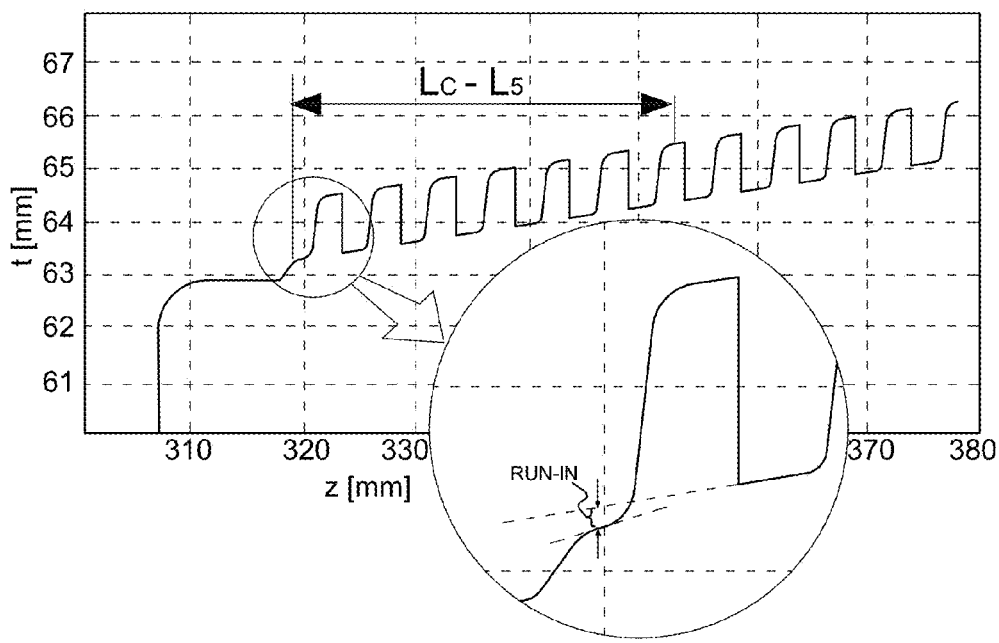
FIG. 14 is a graph illustrating the results of thread run-in scans.

In further embodiments, the measurement method may provide another operation in the data analysis procedure for run-in evaluation. The run-in evaluation may be derived from a longitudinal scan done in respect of the thread reference frame. FIG. 14 illustrates one of these scans and details the region in which the run-in is calculated.

First, a linear fit may be performed with unfiltered root data points between $L_5$+ pitch and $L_c$. This fitted line may be compared with the root data included in the segment given by $R_v$ and $R_{v2}$ as shown in FIG. 5 and referred to as $L_5$. A linear fit may be performed over the error array resulting from that comparison. The difference between this fitting, evaluated at the root mid segment value, and the previous fitting may be set as the run-in value.

A run-out analysis may be carried out in a similar manner to the operation performed for the run-in.

In further embodiments, the measurement method may provide another operation is a pitch determination. In the pitch determination, the load flanks generated from the longitudinal scans may be analysed.

The vectors containing the load flank values for each longitudinal scan may be truncated so as to keep the flanks between $L_5$+ pitch and $L_c$. Of these flanks, just the flanks of type 0 may be accepted. The remainder of the types may be discarded, being considered unreliable as real load flank identifications.

Figure 15:
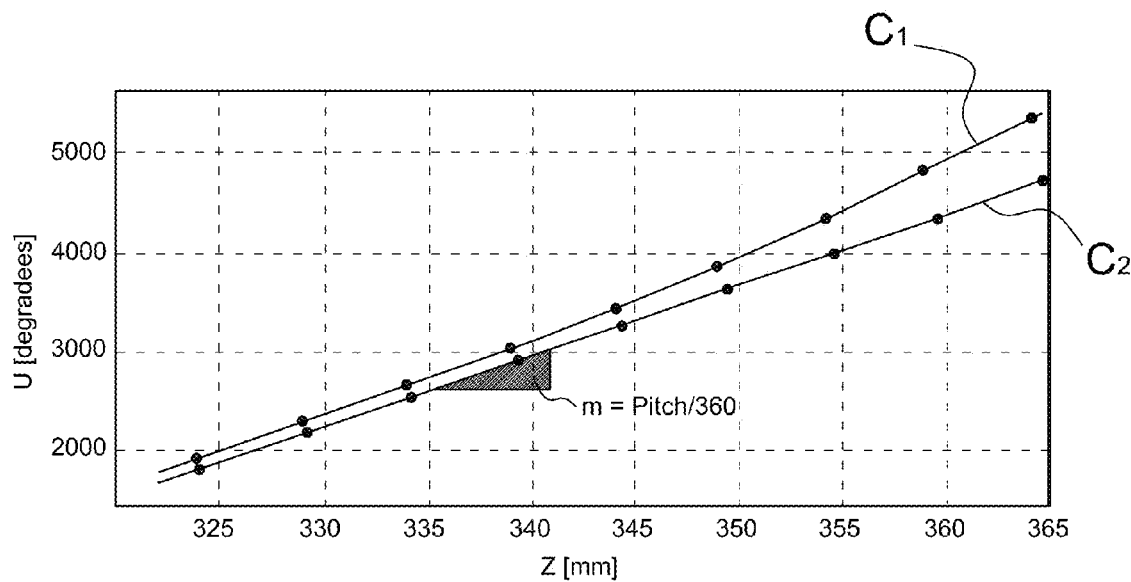
FIG. 15 is a graph illustrating results provided by an embodiment of the disclosed measurement procedure.

FIG. 15 illustrates a hypothetical longitudinal scan and the positions of the load flanks identified. The curve $C_1$ illustrates how the longitudinal scan would appear if expressed in a reference frame of the measurement device 1 where the effect of misalignment is noticed in the curvature (quadratic form) of the flank position trend, due to "falling-off" of the thread generatrix. This effect is also visible in the increasing separation between flank positions as the Z scan position grows.

To calculate the thread pitch, data is transformed to the thread reference frame, indicated by $C_2$ in FIG. 15. Data expressed in the thread reference frame possess a linear trend where the flank positions may not be equally spaced but the slope of the linear fit is the thread pitch.

There are two types of pitch that are calculated and obtained by the software:

A first pitch calculated from the slope of the linear fit for all the flanks detected.

A second pitch calculated from the slope of the line formed by two flanks whose separation depends on the thread being analysed (this measurement must be done in relation to the number of threads per inch).

It may be appreciated that the data obtained in this manner provides information on the pitch for each longitudinal scan.

Embodiments of the disclosed measurement method may be particularly advantageous for measuring threading having a wedge profile. Wedge profiles are profiles that demonstrate a progressive increase in tooth width and more particularly when the wedge profile is combined to a dove-tail shaped tooth profile in an axial section.

In the case of a wedge thread with a dove-tail tooth profile, the measurement of crests and roots may provide for a spiral scan, as described above, where the spiral trajectory follows a line corresponding to the middle position set along the middle distance between the load and stabbing flanks or any other spiral trajectory parallel to said middle position.

In state-of-the-art methods, the measuring and controlling of wedge threads also provides that all measurements are taken from a reference point that is conventionally called bolt point. The bolt point is determined by passing a bolt, such as a measurement element having a small rolling ball of predetermined diameter along the roots. The bolt point is set at the point where the bolt remains stuck in the root, as the tooth width is variable along the thread. The distance and generatrix at which the bolt point is located with respect to the front of the tube determine the reference point for measuring all parameters of a wedge thread.

In certain embodiments of the measurement method, however, setting the bolt point does not need to be performed because the threading parameters are measured from a reference point that is located at the end of the tube.

The determination of the bolt point according to embodiments of the present disclosure, is based on detecting all load and stabbing flanks in the spatial reference system of the measurement device (X, Y, Z). The load and stabbing flanks are further expressed in the spatial reference system (X', Y', Z') of the pin 3 using the axes transformation matrix. This transformation matrix converts the data retrieved from one spatial reference system to the other spatial reference system, as described above.

Once the flanks positions are expressed in the spatial reference system (X', Y', Z') of the pin 3, a linear fit may be performed on the "Zr-Ur" plane where Zr is the axial position of the flank and Ur is the flank generatrix. This linear fitting may be performed for all load and stabbing flanks of the threading separately.

Finally, a subtraction is performed between the two lines adjusted, described in the previous paragraph. The "root width" for the whole thread is obtained and examined for the value (Zr-Ur) of "root valley" where the bolt is stuck in the root for a wedge effect.

Embodiments of the measurement method for wedge profiles may also include a "Higbee" measurement. The Higbee is generally understood by those of skill in the art as the cut of the first incomplete thread adjacent to the bevel made at the nose of the pin where its intersection with the thread load flank makes a sharp edge. The Higbee may correspond to the removal of the incomplete starting thread (of many types of thread, not only wedge) on tube end, with outer diameter OD≥5 in. The Higbee may remove the starting thread from where thread height is about zero, until the thread crest starts. That is to say, until the position where the thread height reaches the acceptance value. The intersection between the Higbee and the crest of the thread defines a line, parallel to the taper. The arc length of the Higbee is approximately 180°.

The Higbee length and height are configured to meet fabrication tolerances and depend on the OD and type of connection. In certain embodiments, the Higbee height can be about 0. That is to say, the machining tool can reach the root of the thread.

Figure 17:
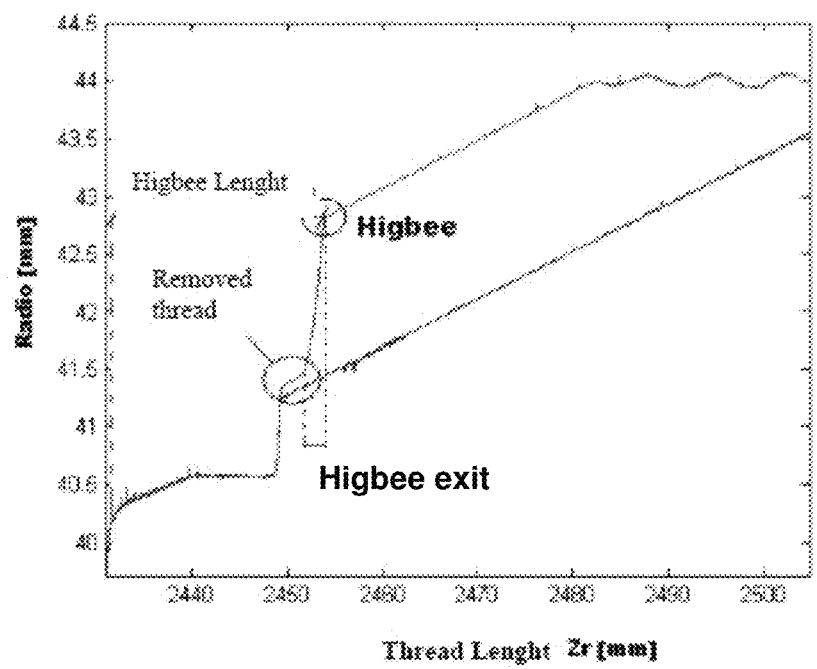
FIG. 17 is a graph illustrating results of another thread scan.

The Higbee point detection may be made by adjusting data retrieved from the spiral scan performed on the crest of threading. The adjusted data may be fit to a line and then eliminating from points that are in an area close to the Higbee from the line when the error between the fitted line and data is greater than some threshold. This point is shown in the graph of FIG. 17.

The order in which the operations described above are made can vary, as well as the number of operations, depending on the necessities and on the parameters to be measured. The completeness of the measurement operation provides also for a calibration of the measurement device before starting operation of the system after set up.

Figure 16:
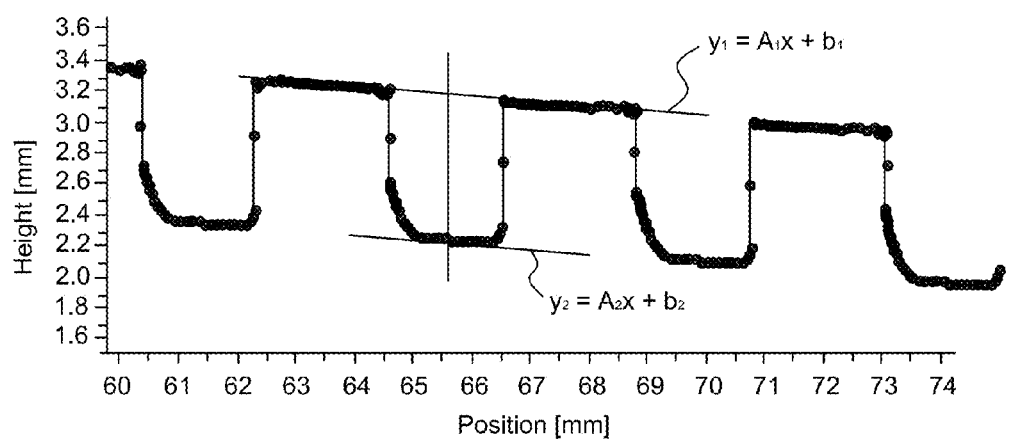
FIG. 16 is a graph illustrating a step height calculation on a thread using linear fitting of crests and roots.

In further embodiments of the measurement method, the data points obtained in the longitudinal scan can be analyzed to obtain the value of the step height. Data close to the edges may be discarded and a linear fit between consecutive crests may be performed (FIG. 16). The fit is compared to the linear fit of the root and its depth is evaluated by calculating the distance between the line $y_2$ at the center of the root. A similar procedure may be performed to calculate the height of the crests, taking $y_1$ as the center of the crest. From the depth and height of the roots and crests, the average and standard deviation may be calculated, the incomplete steps may be identified, and the length of the thread may be estimated.

In an alternative embodiment of the step height calculation, step height may be calculated in a global manner. For example, a linear fit obtained from the crest may be subtracted from root spiral trajectories. This operation gives the difference between the inner and outer cones that represents the value of the step height.

All variants of the measurement method above described can be applied to a pin having a coating and to a pin before coating. The disclosed embodiments may also be used for measurement of box female threadings, regardless of the presence or absence of a coating, by using an appropriate measurement apparatus of the kind described above and having sensors placed on supports of shape and dimensions appropriate to be inserted inside a pipe.

Processes described herein may be embodied in, and fully automated via, software code modules executed by one or more general purpose computers or processors. The code modules may be stored in any type of computer-readable medium or other computer storage device. Some or all the methods may alternatively be embodied in specialized computer hardware. In addition, the components referred to herein may be implemented in hardware, software, firmware, or a combination thereof.

Conditional language such as, among others, "can," "could," "might," or "may," unless specifically stated otherwise, are otherwise understood within the context as used in general to convey that certain embodiments include, while other embodiments do not include certain features, elements, and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

The above mentioned objects and others, which will become apparent in view of the following description, may be achieved according to embodiments of the present disclosure. In an embodiment, a method for measurement of thread parameters of a threaded object coated by at least one layer is provided. The method may include identifying the shape of the threaded object. For example, a measurement device may be provided that includes at least one optical sensor adapted to identify the shape of the threaded object. In certain embodiments, the threaded object may further possess a nose. The method may also include defining a first spatial reference system comprising first co-ordinate axes and defining a second spatial reference system comprising second co-ordinate axes. The method may additionally include determining a quadratic form that represents the threaded object in the second spatial reference system. In certain embodiments, computer means may be provided for storing a preset algorithm that calculates a first matrix describing the quadratic form of the threaded object in the second spatial reference system. In this manner, the relationship between the first and second spatial reference systems may be provided.

In an embodiment, a method for measuring thread parameters of a threaded object may comprise:
a) Defining at least one trajectory of on the surface of threaded object that includes at least one thread of the threaded object. Measurement points may be selected such that the matrix evaluated on these values has maximum rank. For example, the at least one trajectory may be one or more trajectories to be followed by at least one optical sensor.
b) Measuring a position of one or more threads of the threaded object along the at least one trajectory at the measurement points in a second spatial reference system comprising second coordinate axes. For example, a first scanning operation may be performed by the at least one optical sensor along said at least one trajectory and retrieving data of the predefined measurement points.
c) Relating a first spatial reference system to the second spatial reference system so as to determine the relative position of the threaded object with respect to the second spatial reference system. For example, the measured position data may be provided to an algorithm and an axis transformation matrix may be calculated to determine the relationship between the first and second spatial reference systems.
d) Converting all positions represented in the second spatial reference system to the first spatial reference system to provide first measurement result set.
e) Placing at least one layer of a coating material on at least a selected portion of the surface of the threaded object.
f) Measuring a position of the coated, threaded object along at least one of the at least one trajectories in the second reference system and calculating the corresponding position in the first reference system to provide a second measurement result set.
g) comparing first and second measurement results, whereby the thickness of the coating at all measurement points is calculated.

In the following description, the term trajectory may adopt its ordinary meaning and may further include the path a sensor follows through space, describing a sequence of values of the surface location with respect to the sensor.

Embodiments of the methods disclosed herein may achieve several advantages:

In one aspect, employing the method on coated threaded joints may provide measurements that are precise and performed automatically.

In another aspect, measurements may be performed using non-contact sensors (e.g., lasers or other optical sensors). As a result, there is substantially no contact between the coated surface and the measuring instrument and the likelihood of damaging the coated surface during the measurement operation may be significantly reduced.

In a further aspect, quantitative information about characteristics of the threads of the threaded object may be determined. Examples may include, but are not limited to, taper, seal diameter and ovality, run-in, run-out, thread diameter and ovality, pitch along a plurality of generatrices of the tube, and step height, In an additional aspect, measurements may be performed on several threading parameters and tube features regardless of misalignment between the threaded tube and the sensor.

In another aspect, the object to be measured may be precisely located in space by scanning and fitting steps performed, regardless of its position and alignment with respect to the measurement device.

Advantageously, the frame of reference of the threads may be detected independently of the position that the threaded object with respect to the sensor and the condition of coated and uncoated surface. This allows the same trajectory to be followed when performing the measurements before and after the coating of the threaded object.

In further advantage, the quality of a coating deposition process can be verified and assessed at the same time that the geometrical parameters of coated threaded objects are measured. For example, the presence of the coating on the threaded object, as well as the relative uniformity of the thickness of the coating may be determined. Existing methods capable of measure coating thickness are not designed to measure the dimensional tolerances of the thread. In contrast, embodiments of the methods disclosed herein may address both issues, measuring the coating in a non-destructive manner as well as the final dimensional tolerances of the thread.

It should be emphasized that many variations and modifications may be made to the above-described embodiments, the elements of which are to be understood as being among other acceptable examples. All such modifications and variations are intended to be included herein within the scope of this disclosure and protected by the following claims.

Although the foregoing description has shown, described, and pointed out the fundamental novel features of the present teachings, it will be understood that various omissions, substitutions, and changes in the form of the detail of the apparatus and method as illustrated, as well as the uses thereof, may be made by those skilled in the art, without departing from the scope of the present teachings. Consequently, the scope of the present teachings should not be limited to the foregoing discussion, but should be defined by the appended claim.

What is claimed is:

1. A method of measuring thread parameters of a threaded object coated by at least one layer of coating material, comprising:
   obtaining a shape of the threaded object including a nose;
   identifying a first spatial reference system for the threaded object comprising first co-ordinate axes X', Y', Z';
   identifying a second spatial reference system comprising second co-ordinate axes X, Y, Z;
   determining at least one trajectory on the threaded object in the second spatial reference system, the trajectory including selected measurement points;
   obtaining first position data for the threaded object at the predefined measurement points of the at least one trajectory in the second spatial reference system;
   converting the first position data for the threaded object from the second spatial reference system to the first spatial reference system to yield first measurement results;
   coating at least a portion of the threaded object with a selected coating;
   obtaining second position data for the coated, threaded object at the predefined measurement points of the at least one trajectory in the second spatial reference system;
   converting the second position data for the coated, threaded object from the second spatial reference system to the first spatial reference system to yield second measurement results; and
   determining the thickness of the coating from a comparison of the first and second measurement results.

2. The method of claim 1, wherein the obtained position data is converted from the second spatial reference system to the first spatial reference system by applying a transformation matrix to the obtained position data, wherein the transformation matrix that relates the first spatial reference system to the second spatial reference system to the obtained position data.

3. The method of claim 2, wherein the predefined measurement points are selected such that the transformation matrix evaluated on these values has maximum rank.

4. The method of claim 2, wherein the transformation matrix describes the quadratic form representing the threaded object in the second spatial reference system.

5. The method of claim 1, wherein one or more of the at least one trajectory is parallel to the Z axis of the second spatial reference system.

6. The method of claim 1, wherein one or more of the at least one trajectories comprises a helicoidal trajectory.

7. The method of claim 1, wherein at least one of the first and second position data comprises the position of at least one thread flank.

8. The method of claim 7, further comprising determining a helicoidal thread lead trajectory passing along a middle point of one or more of a crests and roots of the threaded object from the position of the at least one thread flank.

9. The method of claim 8, wherein one or more of the at least one trajectory comprises the helicoidal thread lead trajectory.

10. The method of claim 9, further comprising:
    fitting the first position data to a linear functional form to determine a linear dependence of the first position data;
    determining a difference between the first position data and the linear fitting to the first position data;
    conducting a Fourier analysis on said difference.

11. The method of claim 10, wherein the difference between the first position data and the linear dependence of the first position data is evaluated at about a start position and a final position of the threaded object.

12. The method of claim 10, wherein the difference between the first position data and the linear dependence of the first position data is evaluated at position intermediate to a start position and a final position of the threaded object.

13. The method of claim 1, further comprising:
    determining a circular trajectory along a metal-to-metal seal diameter in the first spatial reference system; and
    transforming the circular trajectory into the second spatial reference system using the transformation matrix;
    wherein at least one trajectory includes the transformed circular trajectory.

14. The method of claim 1, further comprising:
    determining a helicoidal trajectory is along a metal-to-metal seal diameter in the first spatial reference system; and
    transforming the helicoidal trajectory into the second spatial reference system using the transformation matrix;
    wherein the at least one trajectory includes the transformed helicoidal trajectory.

15. The method of claim 1, further comprising:
    determining a longitudinal trajectory along a run-in measuring point in the first spatial reference system; and
    transforming the longitudinal trajectory into the second spatial reference system;
    wherein the at least one trajectory includes the transformed longitudinal trajectory.

16. The method of claim 1, further comprising:
    determining a longitudinal trajectory is along a run-out measuring point in the first spatial reference system; and transforming the longitudinal trajectory into the second spatial reference system;

wherein the at least one trajectory includes the transformed longitudinal trajectory.

17. The method of claim 1, further comprising:

determining a longitudinal trajectory intersecting one or more flanks of the threads of the threaded object; and fitting the positions of respective flanks as a function of their angular position to a linear functional form.

18. The method of claim 1, further comprising:

determining at least one trajectory that intersects a thread lead;

identifying the respective positions of intersecting points;

determining respective positions of crests and roots of the threaded object;

calculating a first linear fit to the positions of two consecutive crests;

calculating a second fit to the positions of the root between said two consecutive crests;

determining the distance between a first line and a second line given by the first and second linear fit coefficients at a selected location of the threaded object.

19. A measurement device, comprising:

one or more optical sensors configured to:
measure positions of a surface of a threaded object;
obtain a shape of a threaded object including a nose;
identify a first spatial reference system for the threaded object comprising first co-ordinate axes X', Y', Z';
identify a second spatial reference system comprising second co-ordinate axes X, Y, Z; and
obtain position data for the threaded object at predefined measurement points of at least one trajectory in the second spatial reference system;

a moveable mount configured to hold the one or more optical sensors; and a computing device, the computing device configured to:
determine the at least one trajectory on the threaded object in the second spatial reference system, the trajectory including the selected measurement points; and
convert the position data for the threaded object from the second spatial reference system to the first spatial reference system to yield measurement results;

wherein the one or more optical sensors are configured to obtain position data on a coated and uncoated threaded object, and wherein the computing device is configured to determine a thickness of a coating on a threaded object from a comparison between position data obtained on the uncoated threaded object and position data on the coated threaded object.

20. The device of claim 19, wherein the one or more sensors comprises a non-contact laser based sensor.

21. The device of claim 19, further comprising an analysis component configured to receive images of threads of the threaded object and to determine one or more thread characteristics from the received images.

22. The device of claim 21, wherein the thread characteristics comprise one or more of thread taper, seal diameter and ovality, run-in, run-out, thread diameter, pitch along multiple generatrices of the threaded object, and step height.

23. The device of claim 19, wherein the computing device is further configured to convert the obtained position data from the second spatial reference system to the first spatial reference system by applying a transformation matrix to the obtained position data, wherein the transformation matrix that relates the first spatial reference system to the second spatial reference system to the obtained position data.

\* \* \* \* \*

UNITED STATES PATENT AND TRADEMARK OFFICE
CERTIFICATE OF CORRECTION

PATENT NO.        : 8,744,160 B2
APPLICATION NO.   : 13/151202
DATED             : June 3, 2014
INVENTOR(S)       : Bonadeo et al.

Page 1 of 1

It is certified that error appears in the above-identified patent and that said Letters Patent is hereby corrected as shown below:

On the Title Page under Illustrative Figure, Line 12, Change "througt" to --through--, Line 14, Change "througt" to --through--, Line 21, Change "taber" to --Taper--, Line 21, Change "ovalitv" to --ovality--, Line 21, Change "heigth" to --height--.

In the Drawings

Sheet 2 of 10 (Fig. 2) at line 12 (approx.), Change "througt" to --through--.

Sheet 2 of 10 (Fig. 2) at line 14 (approx.), Change "througt" to --through--.

Sheet 2 of 10 (Fig. 2) at line 21 (approx.), Change "Taber" to --Taper--.

Sheet 2 of 10 (Fig. 2) at line 21 (approx.), Change "ovalitv" to --ovality--.

Sheet 2 of 10 (Fig. 2) at line 21 (approx.), Change "heigth" to --height--.

Sheet 3 of 10 (Fig. 3a) at line 1 (approx.), Change "Rest" to --Reset--.

Sheet 10 of 10 (Fig. 17) at line 4 (approx.), Change "Lenght" to --Length--.

Sheet 10 of 10 (Fig. 17) at line 12 (approx.), Change "Lenght" to --Length--.

In the Specification

In column 7 at line 14, Change "(X',Y',Z')" to --(X', Y', Z')--.

In column 16 at line 61, Change "height," to --height.--.

In column 17 at line 35, Change "claim." to --claims.--.

Signed and Sealed this
Twenty-seventh Day of January, 2015

Michelle K. Lee
*Deputy Director of the United States Patent and Trademark Office*